(12) United States Patent
Kawahara et al.

(10) Patent No.: US 10,340,053 B2
(45) Date of Patent: Jul. 2, 2019

(54) RADIATION-IRRADIATION DEVICE

(71) Applicant: FUJIFILM CORPORATION, Minato-ku, Tokyo (JP)

(72) Inventors: Misaki Kawahara, Kanagawa (JP); Koichi Kitano, Kanagawa (JP); Kenji Nakamura, Kanagawa (JP); Masaru Sato, Kanagawa (JP); Masayuki Iwasaka, Kanagawa (JP); Takeyasu Kobayashi, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 15/944,804

(22) Filed: Apr. 4, 2018

(65) Prior Publication Data

US 2018/0301235 A1    Oct. 18, 2018

(30) Foreign Application Priority Data

Apr. 12, 2017   (JP) .................. 2017-078741

(51) Int. Cl.
| | |
|---|---|
| *A61B 5/04* | (2006.01) |
| *A61B 6/06* | (2006.01) |
| *A61B 6/00* | (2006.01) |
| *G21K 1/04* | (2006.01) |
| *A61B 6/08* | (2006.01) |

(Continued)

(52) U.S. Cl.
CPC ................ *G21K 1/046* (2013.01); *A61B 6/06* (2013.01); *A61B 6/08* (2013.01); *A61B 6/107* (2013.01); *A61B 6/40* (2013.01); *A61B 6/4405* (2013.01); *A61B 6/4411* (2013.01); *A61B 6/467* (2013.01); *A61B 6/542* (2013.01); *A61B 6/588* (2013.01); *H01J 35/00* (2013.01)

(58) Field of Classification Search
CPC .. G21K 1/046; A61B 6/06; A61B 6/08; A61B 6/4405; A61B 6/588
USPC ....................................... 250/492.1
See application file for complete search history.

(56) References Cited

U.S. PATENT DOCUMENTS 7,102,818 B2 *  9/2006  Sander ................ G02B 21/082
                                                    359/368
7,327,456 B1 *  2/2008  Woollam .................. G01J 1/02
                                                    356/364

(Continued)

FOREIGN PATENT DOCUMENTS

JP          2014-533586 A       12/2014

*Primary Examiner* — Nicole M Ippolito
(74) *Attorney, Agent, or Firm* — Solaris Intellectual Property Group, PLLC (57) ABSTRACT

The radiation-irradiation device includes: a radiation generating unit that generates radiation; a collimator unit that controls an irradiation range to be irradiated with the radiation generated by the radiation generating unit; and an interval ensuring unit that includes a contact member being in contact with a subject to be irradiated with the radiation in a case in which a distance between the radiation generating unit and the subject is shorter than a preset distance, and ensures an interval between the radiation generating unit and the subject. The interval ensuring unit is detachably mounted on the collimator unit and is capable of being mounted at different rotational positions about an axis, which passes through a center of a diaphragm of the collimator unit and extends in the direction of an optical axis of the radiation, as a central axis.

7 Claims, 6 Drawing Sheets

(51) Int. Cl.
*A61B 6/10* (2006.01)
*H01J 35/00* (2006.01)

(56) References Cited

U.S. PATENT DOCUMENTS

2009/0244545 A1* 10/2009 Toida .................. A61B 5/0066
356/477
2016/0313233 A1* 10/2016 Zangmeister ...... G01N 21/1702

* cited by examiner

RADIATION-IRRADIATION DEVICE

CROSS REFERENCE TO RELATED APPLICATIONS

The present application claims priority under 35 U.S.C. § 119 to Japanese Patent Application No. 2017-078741 filed on Apr. 12, 2017. The above application is hereby expressly incorporated by reference, in its entirety, into the present application.

BACKGROUND

Technical Field

The present invention relates to a radiation-irradiation device that is used in radiography, and more particularly, to a portable radiation-irradiation device.

Related Art

Various portable (transportable) radiation-irradiation devices, which are used at home, in a disaster area, and the like, have been proposed in recent years (for example, JP2014-533586A).

Generally, such a portable radiation-irradiation device includes a radiation generating unit that includes a radiation source, a collimator unit that controls an irradiation range to be irradiated with radiation emitted from the radiation generating unit, and an interval ensuring unit that is used to ensure an interval between the radiation generating unit and a patient. The interval ensuring unit is also called a skin guard; ensures the interval between the radiation generating unit and the patient so that the radiation generating unit does not approach the patient more than necessary; and includes members that are in contact with the patient so that the radiation generating unit does not approach the patient any more in a case in which the radiation generating unit approaches the patient.

Further, all of the radiation generating unit, the collimator unit, and the interval ensuring unit having been described above are integrally formed in the portable radiation-irradiation device in the related art.

However, since the size of the entire device is increased in a case in which all of the radiation generating unit, the collimator unit, and the interval ensuring unit are integrally formed as described above, there is a problem that the storage efficiency and transportability of the device are not good.

Further, the interval ensuring unit ensures the interval between the radiation generating unit and a patient as described above. On the other hand, in a case in which, for example, an imaging place is a narrow place, the members of the interval ensuring unit may come into contact with persons or objects positioned therearound and may be obstructive.

SUMMARY

The invention has been made in consideration of the above-mentioned problems, and an object of the invention is to provide a radiation-irradiation device of which storage efficiency and transportability can be improved and which is easily handled even at a narrow place.

A radiation-irradiation device of the invention comprises: a radiation generating unit that generates radiation; a collimator unit that controls an irradiation range to be irradiated with the radiation generated by the radiation generating unit; and an interval ensuring unit that includes a contact member being in contact with a subject to be irradiated with the radiation in a case in which a distance between the radiation generating unit and the subject is shorter than a preset distance, and ensures an interval between the radiation generating unit and the subject. The interval ensuring unit is detachably mounted on the collimator unit and is capable of being mounted at different rotational positions about an axis, which passes through a center of a diaphragm of the collimator unit and extends in the direction of an optical axis of the radiation, as a central axis.

Further, in the radiation-irradiation device of the invention, the interval ensuring unit may be capable of being mounted at any rotational position about the central axis.

Furthermore, in the radiation-irradiation device of the invention, the interval ensuring unit may include a base part on which the contact member is provided and which is installed around an emission port of the collimator unit for the radiation, and the base part may include an opening that limits an irradiation range to be irradiated with radiation emitted from the emission port of the collimator unit.

Moreover, in the radiation-irradiation device of the invention, the contact member may be provided at a position along a plane that is formed by connecting an edge of an opening, which is obtained in a case in which the diaphragm of the collimator unit is largest, to an edge of the opening of the base part.

Further, in the radiation-irradiation device of the invention, the contact member may be formed of a columnar member and the interval ensuring unit may include a columnar connection member that connects the contact member to the base part, and the connection member may be disposed on a plane formed by extending a lower surface of a housing of the radiation generating unit in the direction of the optical axis of the radiation in a case in which the interval ensuring unit is installed on the collimator unit so that an extending direction of the contact member is a vertical direction.

Furthermore, in the radiation-irradiation device of the invention, the interval ensuring unit may be adapted to be detachably mounted on the collimator unit by magnets.

Moreover, the radiation-irradiation device of the invention may further comprise an emission control unit that stops emission of the radiation in a case in which the interval ensuring unit is detached from the collimator unit.

The radiation-irradiation device of the invention includes: a radiation generating unit that generates radiation; a collimator unit that controls an irradiation range to be irradiated with the radiation generated by the radiation generating unit; and an interval ensuring unit that includes a contact member being in contact with a subject to be irradiated with the radiation in a case in which a distance between the radiation generating unit and the subject is shorter than a preset distance, and ensures an interval between the radiation generating unit and the subject.

Further, since the interval ensuring unit is detachably mounted on the collimator unit, the storage efficiency and transportability of the radiation-irradiation device can be improved. Furthermore, since the interval ensuring unit is capable of being mounted at different rotational positions about an axis, which passes through a center of a diaphragm of the collimator unit and extends in the direction of an optical axis of the radiation, as a central axis, the interval ensuring unit can be rotated not to be in contact with persons or objects, which are positioned therearound, even though an imaging place is small. Accordingly, the radiation-irradiation device can be easily handled.

DETAILED DESCRIPTION

Figure 1:
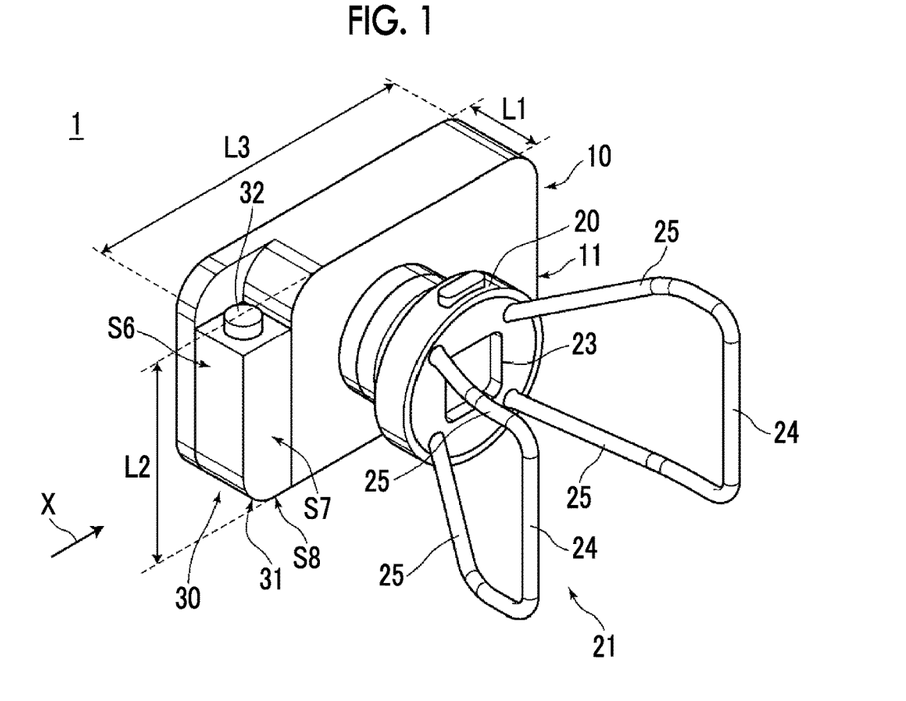
FIG. 1 is a perspective view showing the appearance of an embodiment of a radiation-irradiation device of the invention.

An embodiment of a radiation-irradiation device of the invention will be described in detail below with reference to the drawings. The radiation-irradiation device of this embodiment is a portable radiation-irradiation device that is mainly used at home, in a disaster area, and the like. FIG. 1 is a perspective view showing the appearance of the radiation-irradiation device 1 of this embodiment. Further, FIG. 2 is a diagram showing the side appearance of the radiation-irradiation device 1 of FIG. 1 that is viewed in the direction of an arrow X.

As shown in FIG. 1, the radiation-irradiation device 1 of this embodiment includes a radiation generating unit 10, a collimator unit 20, an interval ensuring unit 21, and an exposure switch unit 30.

The radiation generating unit 10 includes a radiation source 14 (see FIG. 6), such as an X-ray tube, which generates radiation, and emits radiation that is generated by the radiation source. The radiation generating unit 10 includes a housing 11, and the radiation source 14 and the like are received in the housing 11. The housing 11 is formed in the shape of a rectangular parallelepiped, and is formed so that the length L1 of a first side extending in the direction of the optical axis of radiation is shorter than the length L2 of a second side orthogonal to the first side and the length L3 of a third side orthogonal to the first side. Further, it is preferable that a relationship among the length L1 of the first side, the length L2 of the second side, and the length L3 of the third side satisfies "L1<L2<L3". Furthermore, it is preferable that a ratio between the length L1 of the first side and the length L3 of the third side is in the range of 1:1 to 1:6, and it is preferable that a ratio between the length L1 of the first side and the length L2 of the second side is in the range of 1:1 to 1:6. The transportability of the radiation-irradiation device 1 and the usability of the radiation-irradiation device 1 during use can be improved in a case in which the lengths of the housing 11 of the radiation generating unit 10 are set to the above-mentioned ratios. It is preferable that the length L1 of the first side is set to 80 mm or less.

Figure 2:
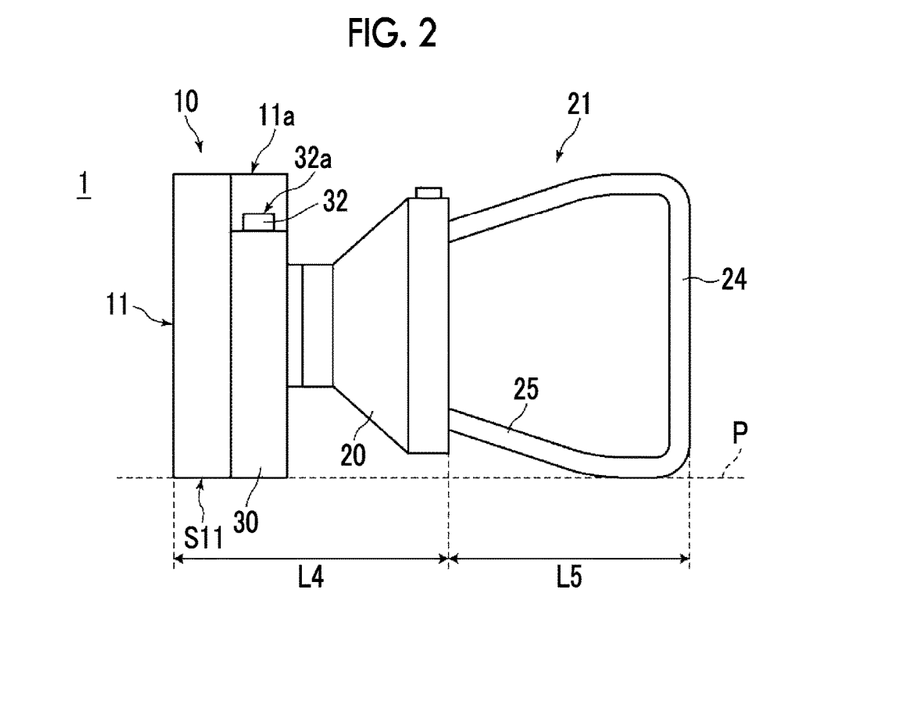
FIG. 2 is a diagram showing the side appearance of the radiation-irradiation device of FIG. 1 that is viewed in the direction of an arrow X.

Further, it is preferable that a ratio between the length L4 of the radiation generating unit 10 and the collimator unit 20 in the direction of the optical axis of radiation and the length L5 of the interval ensuring unit 21 in the direction of the optical axis is set in the range of 1:2 to 3:1 as shown in FIG. 2. The length of the interval ensuring unit 21 is a distance between the end face of the collimator unit 20 in the direction of the optical axis and a contact member 24 of the interval ensuring unit 21. Accordingly, it is possible to reduce the size of the radiation-irradiation device 1 and to ensure an interval between the radiation generating unit 10 and a patient.

The collimator unit 20 controls the irradiation range for a patient that is to be irradiated with radiation generated by the radiation generating unit 10. The collimator unit 20 includes a diaphragm 26 (see FIG. 6), and the irradiation range for the patient, which is to be irradiated with radiation, is controlled by a change in the size of the diaphragm 26. The size of the diaphragm 26 is adapted to be capable of being manually changed by a user.

Figure 3:
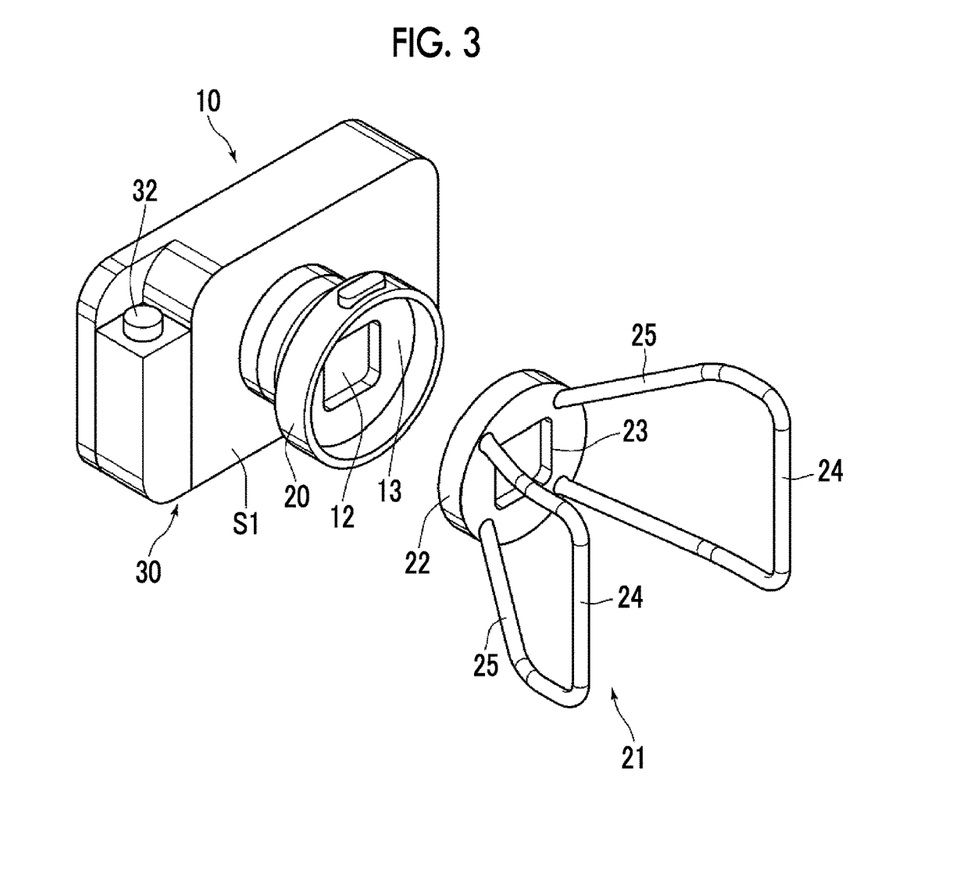
FIG. 3 is a diagram showing a state in which an interval ensuring unit is detached from a collimator unit of the radiation-irradiation device.

Since a rectangular emission port 12 from which radiation generated by the radiation generating unit 10 is emitted is formed at the collimator unit 20 as shown in FIG. 3, radiation, which passes through the diaphragm 26 of the collimator unit 20, is emitted from the emission port 12.

The interval ensuring unit 21 is adapted to be detachably mounted on the collimator unit 20 as shown in FIG. 3. An installation portion 13 on which the interval ensuring unit 21 is detachably installed is formed around the emission port 12 of the collimator unit 20. Since the installation portion 13 is provided with a magnet of which the pole is opposite to the pole of a magnet provided on a base part 22 of the interval ensuring unit 21, the interval ensuring unit 21 is adapted to be detachably mounted on the installation portion 13 by the magnetic forces of the magnets. Since the interval ensuring unit 21 is adapted to be detachably mounted on the collimator unit 20 in this way, the transportability and storage efficiency of the radiation-irradiation device 1 can be improved.

As shown in FIG. 3, the interval ensuring unit 21 includes the base part 22, contact members 24, and connection members 25. Each of the contact members 24 is formed of a columnar member, and is a member that is in contact with a patient in a case in which a distance between the radiation generating unit 10 and the patient (subject) to be irradiated with radiation is shorter than a preset distance. An interval between the radiation generating unit 10 and the patient is ensured in a case in which the contact members 24 are in contact with the patient.

Each of the connection members 25 is formed of a columnar member, and connects the contact member 24 to the base part 22. Four connection members 25 are provided on the base part 22, and are members that extend from the base part 22 in the emission direction of radiation. Further, the contact member 24 is provided between distal end portions of a set of two connection members 25.

Figure 4:
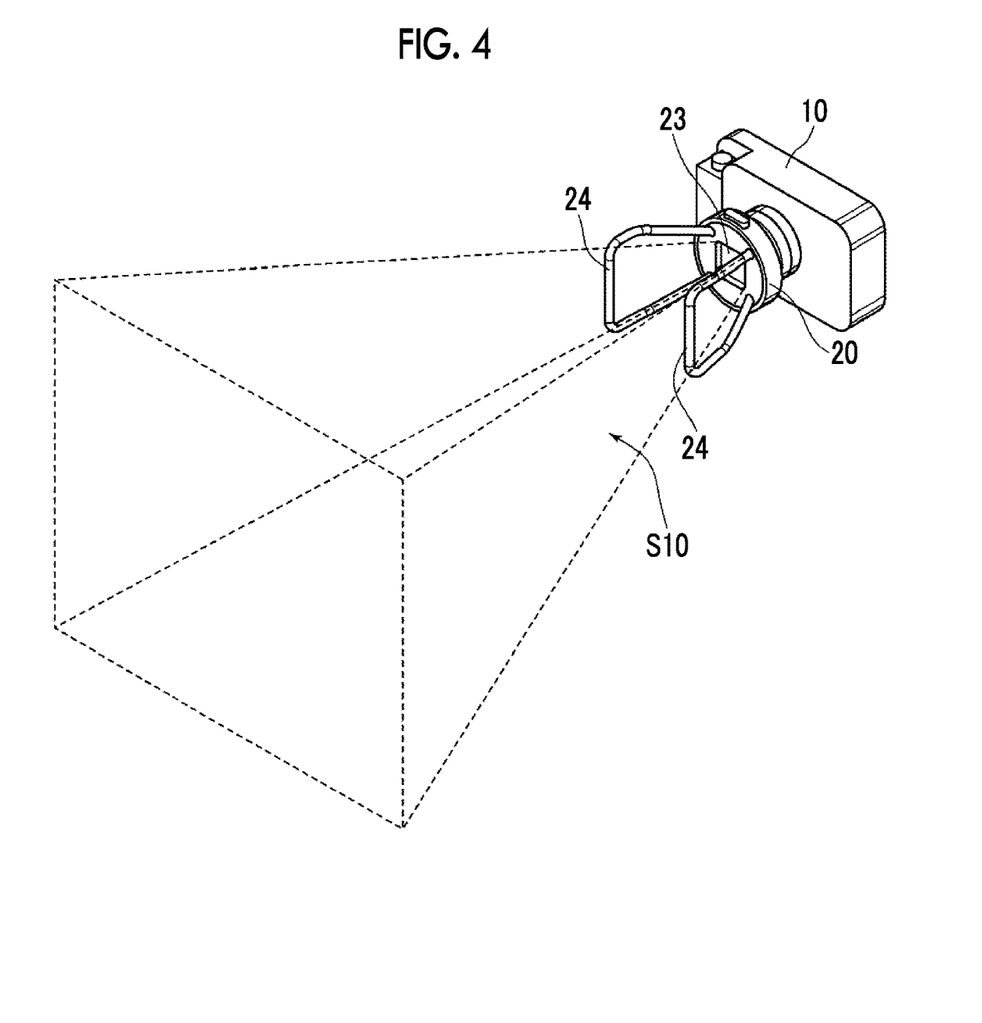
FIG. 4 is a diagram illustrating the arrangement of contact members.
Figure 5A:
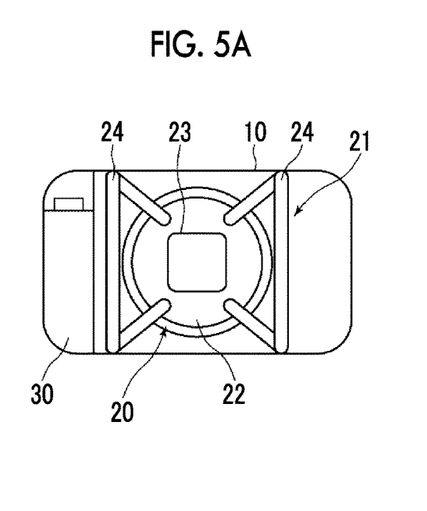
FIGS. 5A to 5D are diagrams showing four states in which the interval ensuring unit is mounted on the collimator unit.
Figure 5B:
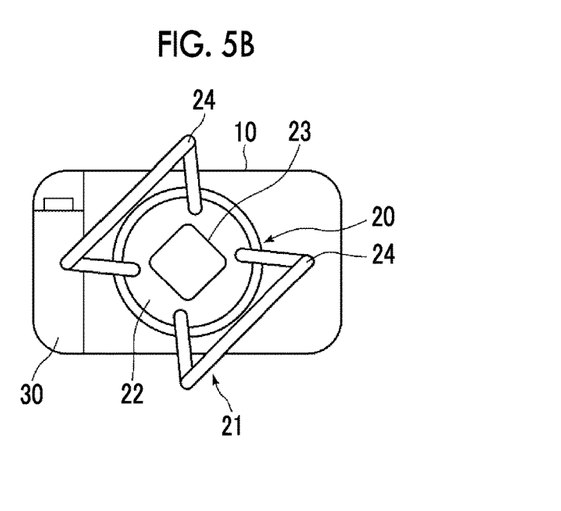
Figure 5C:
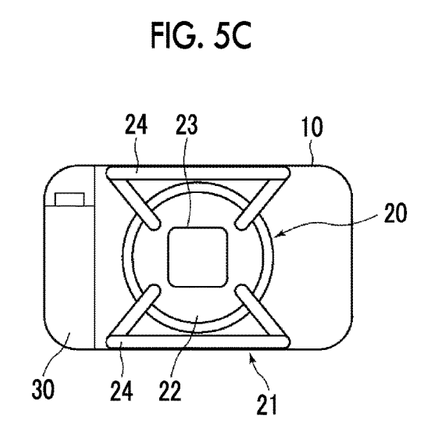
Figure 5D:
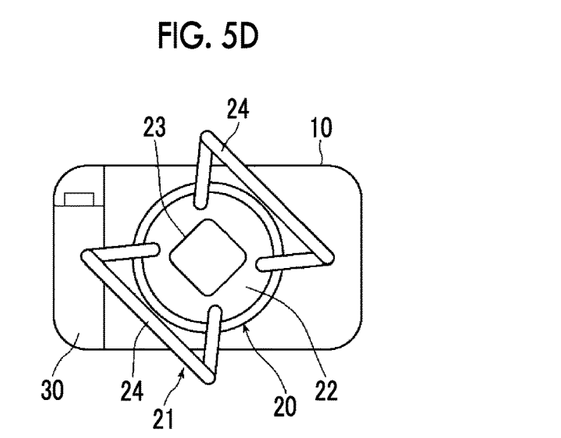

As shown in FIG. 1, the four connection members 25 are formed so that an interval between the connection members 25 is increased toward a patient from the collimator unit 20. Further, as shown in FIG. 4, each of the contact members 24 is provided at a position along a plane S10 that is formed by connecting the edge of an opening, which is obtained in a case in which the diaphragm 26 of the collimator unit 20 is largest, to the edge of an opening 23 of the base part 22. According to this structure, a rectangular range, which is formed by four end portions of the two contact members 24, can be set to the same range as a range to which radiation is emitted and can be set to the necessary minimum size. Accordingly, the size of the interval ensuring unit 21 can be reduced.

Furthermore, it is preferable that the connection members 25 are formed so that a lower surface S11 of the housing 11 of the radiation generating unit 10 is disposed on a plane P extending in the direction of the optical axis of radiation as shown in FIG. 2 in a case in which the interval ensuring unit 21 is installed on the collimator unit 20 so that the extending direction of the contact member 24 is a vertical direction. Accordingly, in a case in which the radiation-irradiation device 1 is placed on a predetermined plane, a part of the connection members 25 and the plane are in contact with each other. Therefore, the radiation-irradiation device 1 can be supported, so that the fall of the radiation-irradiation device 1 can be prevented.

The base part 22 is to be installed on the installation portion 13 of the collimator unit 20, and is provided with the magnet of which the pole is opposite to the pole of the magnet provided on the installation portion 13. Further, the opening 23 through which radiation emitted from the emission port 12 of the collimator unit 20 passes is formed at the base part 22 as described above, and a patient is irradiated with radiation emitted from the opening 23. The irradiation range for the patient, which is to be irradiated with radiation emitted from the emission port 12 of the collimator unit 20, is limited by the opening 23 of the base part 22.

FIGS. 5A to 5D are diagrams showing four states in which the interval ensuring unit 21 is mounted on the collimator unit 20. In this embodiment, the interval ensuring unit 21 is adapted to be detachably mounted on the collimator unit 20 by the magnets as described above. Accordingly, as shown in FIGS. 5A to 5D, the interval ensuring unit 21 is adapted to be capable of being mounted on the collimator unit 20 at any rotational position about an axis, which passes through the center of the diaphragm 26 of the collimator unit 20 and extends in the direction of the optical axis of radiation, as a central axis.

According to this structure, the interval ensuring unit 21 can be easily mounted on and detached from the collimator unit 20. Further, since the orientation of the extending direction of the contact member 24 with respect to the central axis can be changed, it is possible to avoid the contact between the contact members 24 and persons or objects, which are positioned around the contact members 24, by rotating the interval ensuring unit 21 according to the usage condition. Furthermore, since the orientation of the opening 23 of the interval ensuring unit 21 with respect to the central axis can be changed, the irradiation range to be irradiated with radiation can be changed. Accordingly, the operability of the radiation-irradiation device can be improved.

Figure 6:
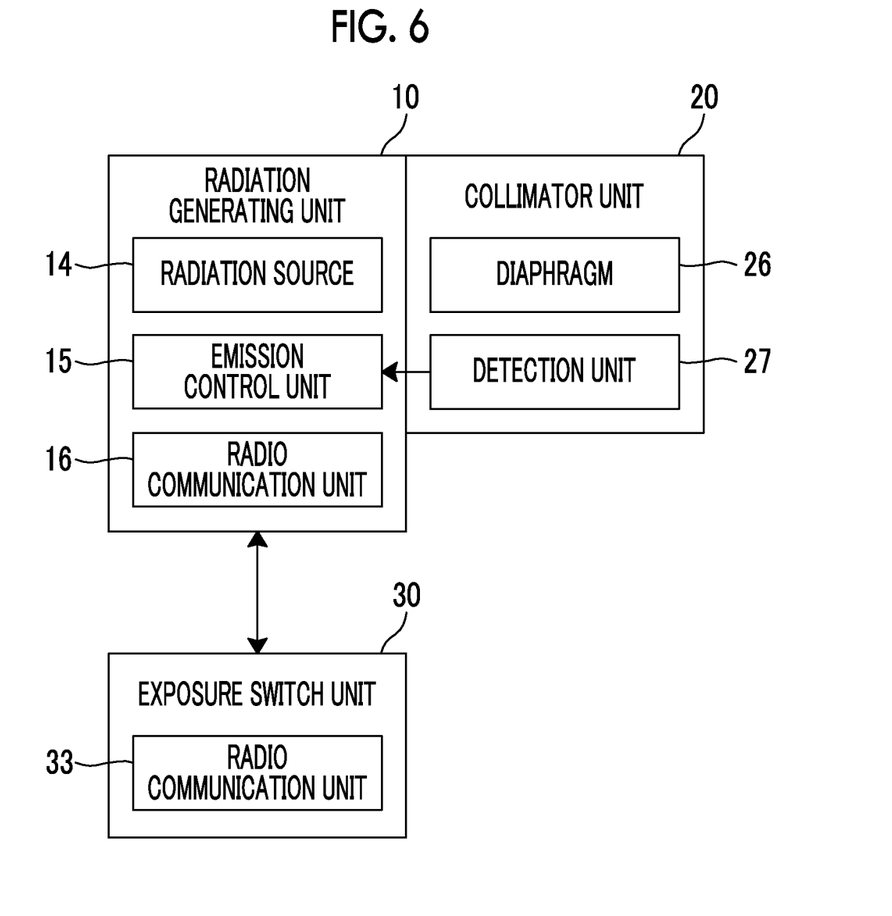
FIG. 6 is a schematic diagram showing the internal configuration of a radiation generating unit, the collimator unit, and an exposure switch unit.

FIG. 6 is a schematic diagram showing the internal configuration of the radiation generating unit 10, the collimator unit 20, and the exposure switch unit 30. The above-mentioned radiation source 14, an emission control unit 15 that controls the emission of radiation, and a radio communication unit 16 are provided in the housing 11 of the radiation generating unit 10. Further, the above-mentioned diaphragm 26 and a detection unit 27 are provided in the collimator unit 20, and a radio communication unit 33 is provided in the exposure switch unit 30.

The emission control unit 15 of the radiation generating unit 10 stops the emission of radiation from the radiation generating unit 10 even though a button 32 of the exposure switch unit 30 is pressed in a case in which the interval ensuring unit 21 is detached from the collimator unit 20. Accordingly, since the radiation-irradiation device 1 has a so-called interlock function, it is possible to prevent erroneous exposure that occurs in a case in which the button 32 is pressed by mistake during the transport and setup of the radiation-irradiation device 1.

Further, the detection unit 27 is provided in the collimator unit 20 to detect the mounting/detachment of the interval ensuring unit 21 on/from the collimator unit 20. The detection unit 27 emits light toward the interval ensuring unit 21, and receives the reflected light thereof. In a case in which the reflected light, which is reflected by the interval ensuring unit 21, is received by the detection unit 27 of the collimator unit 20, the mounting of the interval ensuring unit 21 on the collimator unit 20 is detected. On the contrary, in a case in which a state in which the reflected light reflected by the interval ensuring unit 21 is not received by the detection unit 27 of the collimator unit 20 is detected, the detachment of the interval ensuring unit 21 from the collimator unit 20 is detected.

The mounting/detachment of the interval ensuring unit 21 on/from the collimator unit 20 is detected by using an optical sensor in this embodiment, but the invention is not limited thereto. Proximity sensors, such as other magnetic force sensors, can be used. Further, a mechanical switch may be provided without the use of such a non-contact sensor to detect the mounting/detachment of the interval ensuring unit 21 on/from the collimator unit 20.

The radio communication unit 16 of the radiation generating unit 10 and the radio communication unit 33 of the exposure switch unit 30 communicate with each other by radio. In a case in which the button 32 of the exposure switch unit 30 is pressed, a radio signal is output to the radiation generating unit 10 from the radio communication unit 33 of the exposure switch unit 30 and is received by the radio communication unit 16 of the radiation generating unit 10. In a case in which the radio signal output from the exposure switch unit 30 is received by the radio communication unit 16, the emission control unit 15 of the radiation generating unit 10 controls the radiation source 14 to allow the radiation source 14 to emit radiation.

The interval ensuring unit 21 is adapted to be detachably mounted on the collimator unit 20 by the magnets in the embodiment, but may be adapted to be detachably mounted by providing members, which have adhesiveness, on the attachment/detachment surface of the collimator unit 20 and the attachment/detachment surface of the interval ensuring unit 21. A hook-and-loop fastener (for example, MAGIC TAPE (registered trademark)) and an adhesive tape having adhesiveness may be used as the member having adhesiveness.

Further, the interval ensuring unit 21 may be provided with a protruding portion or a recessed portion and the collimator unit 20 may be provided with a recessed portion or a protruding portion to be fitted to the protruding portion or the recessed portion of the interval ensuring unit 21 so that the interval ensuring unit 21 is adapted to be detachably mounted on the collimator unit 20. In this case, a plurality of combinations of fitting between the protruding portion and the recessed portion may be set so that the interval ensuring unit 21 is adapted to be detachably mounted on the collimator unit 20 at a plurality of different rotational positions. Specifically, the collimator unit 20 and the interval ensuring unit 21 may be provided with combinations of the protruding portion and the recessed portion corresponding to the respective rotational positions. In regard to the structure of the protruding portion and the recessed portion, for example, a groove may be formed as the recessed portion and the protruding portion may be formed in a shape that allows the protruding portion to be fitted to the groove. Furthermore, the protruding portion may be formed of a button that can be biased by an elastic member, such as a spring, so as to be pressed; and the button may be adapted to be pressed in a case in which the interval ensuring unit 21 is to be mounted on/detached from the collimator unit 20 and may be adapted to protrude and be fitted to the recessed portion in a state in which the interval ensuring unit 21 is mounted on the collimator unit 20.

Figure 7:
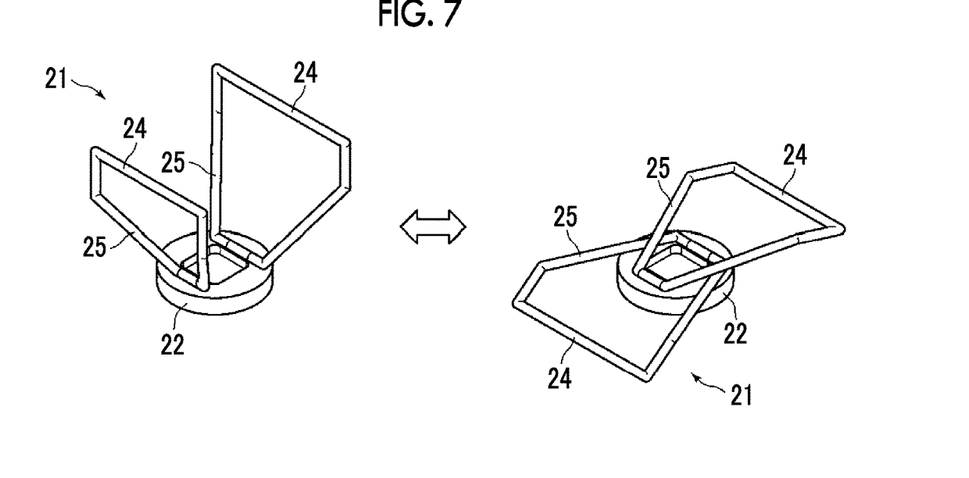
FIG. 7 is a diagram showing an example of the interval ensuring unit that is adapted to be foldable.

Further, the interval ensuring unit 21 may be adapted so that the contact members 24 and the connection members 25 are folded as shown in FIG. 7. Specifically, in the structure shown in FIG. 7, two sets of frame bodies, each of which includes one contact member 24 and two connection members 25 connected to both ends of the contact member 24, are formed so as to have sizes in which one frame body enters the other frame body. Furthermore, the frame bodies are adapted to be folded by rotationally moving about the connecting portions between the frame bodies and the base part 22 as rotational movement axes in a direction in which the frame bodies and the base part 22 face each other. In a case in which the frame bodies are adapted to be foldable as described above, the storage efficiency and transportability of the radiation-irradiation device 1 can be improved.

Figure 8:
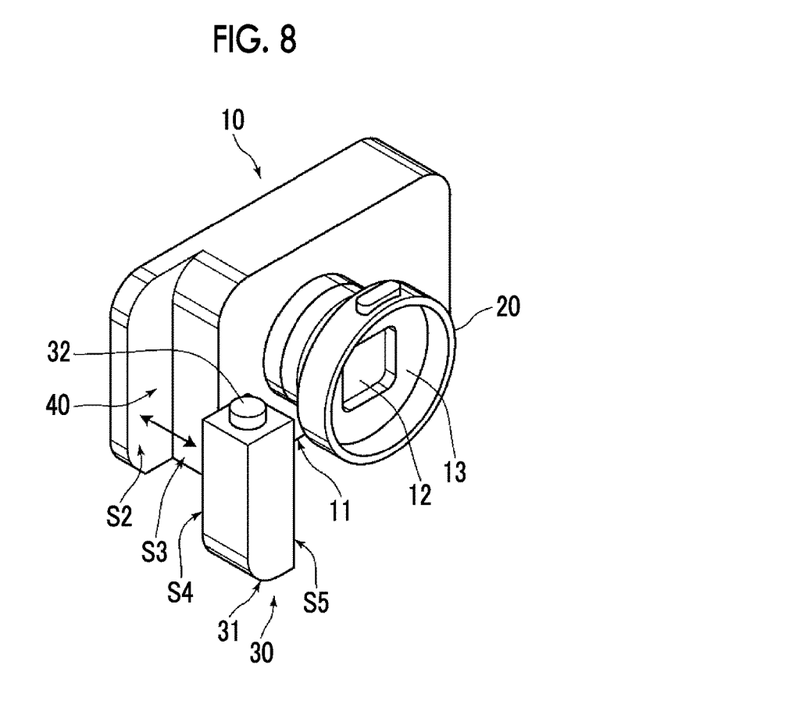
FIG. 8 is a diagram showing a state in which the exposure switch unit is detached from the radiation generating unit.

Next, the structure of the exposure switch unit 30 will be described. As shown in FIG. 8, a recessed portion 40 is formed on the housing 11 of the radiation generating unit 10. The recessed portion 40 is formed by two surfaces S2 and S3 orthogonal to each other, and the exposure switch unit 30 is fitted to the recessed portion 40 formed by the two surfaces. Further, the exposure switch unit 30 includes a housing 31 that is different from the housing of the radiation generating unit 10, and the exposure switch unit 30 is adapted to be detachably mounted on the radiation generating unit 10 through some surfaces of the housings of the exposure switch unit 30 and the radiation generating unit 10.

Specifically, the two surfaces S2 and S3 that form the recessed portion 40 of the housing 11 of the radiation generating unit 10 and two surfaces S4 and S5, which are orthogonal to each other, of the housing 31 of the exposure switch unit 30 form attachment/detachment surfaces; and the exposure switch unit 30 is adapted to be detachably mounted on the radiation generating unit 10 through the respective attachment/detachment surfaces.

Magnets having poles opposite to each other are installed in the housings 11 and 31 near the back sides of the attachment/detachment surfaces of the radiation generating unit 10 and the back sides of the attachment/detachment surfaces of the exposure switch unit 30, and the exposure switch unit 30 is adapted to be detachably mounted on the radiation generating unit 10 by the magnetic forces of the magnets.

Since the exposure switch unit 30 is adapted to be detachably mounted on the radiation generating unit 10 through some surfaces of the housings of the exposure switch unit 30 and the radiation generating unit 10 as described above, the radiation generating unit 10 and the exposure switch unit 30 can be integrally transported together and the exposure switch unit 30 can be easily mounted on and detached from the radiation generating unit 10 by a single operation.

Further, in the radiation-irradiation device 1 of this embodiment, surfaces S6, S7, and S8 of the housing 31 of the exposure switch unit 30 other than the above-mentioned attachment/detachment surfaces S4 and S5 are adapted to be flush with the surfaces of the housing of the radiation generating unit 10 as shown in FIG. 1 in a case in which the exposure switch unit 30 is mounted on the radiation generating unit 10. Specifically, in this embodiment, three surfaces S6, S7, and S8, which are the surfaces of the housing 31 of the exposure switch unit 30 other than the attachment/detachment surfaces S4 and S5 and are orthogonal to each other, are adapted to be flush with the surfaces of the housing 11 of the radiation generating unit. Furthermore, the housing 31 of the exposure switch unit 30 is adapted to form some surfaces and one corner of a rectangular parallelepiped in a state in which the exposure switch unit 30 is mounted on the radiation generating unit 10.

According to this structure, since unnecessarily protruding portions and the like can be removed in a case in which the exposure switch unit 30 is mounted on the radiation generating unit 10, the radiation-irradiation device 1 can be easily handled.

Moreover, for the prevention of the press of the button 32 of the exposure switch unit 30 caused by mistake, it is preferable that an upper surface 32a of the button 32 is positioned below an upper surface 11a of the housing 11 of the radiation generating unit 10 as shown in FIG. 2.

The exposure switch unit 30 is adapted to be detachably mounted on the radiation generating unit 10 by the magnets in the embodiment. However, the detachable structure is not limited thereto, and the exposure switch unit 30 is adapted to be detachably mounted on the radiation generating unit 10 by a mechanical mechanism.

What is claimed is:

1. A radiation-irradiation device comprising:
a radiation generating unit that generates radiation;
a collimator unit that controls an irradiation range to be irradiated with the radiation generated by the radiation generating unit; and
an interval ensuring unit that includes a contact member being in contact with a subject to be irradiated with the radiation in a case in which a distance between the radiation generating unit and the subject is shorter than a preset distance, and ensures an interval between the radiation generating unit and the subject,
wherein the interval ensuring unit is detachably mounted on the collimator unit and is capable of being mounted at different rotational positions about an axis, which passes through a center of a diaphragm of the collimator unit and extends in a direction of an optical axis of the radiation, as a central axis.

2. The radiation-irradiation device according to claim 1, wherein the interval ensuring unit is capable of being mounted at any rotational position about the central axis.

3. The radiation-irradiation device according to claim 1, wherein the interval ensuring unit includes a base part on which the contact member is provided and which is installed around an emission port of the collimator unit for the radiation, and
the base part includes an opening that limits an irradiation range to be irradiated with radiation emitted from the emission port of the collimator unit.

4. The radiation-irradiation device according to claim 3, wherein the contact member is provided at a position along a plane that is formed by connecting an edge of an opening, which is obtained in a case in which the diaphragm of the collimator unit is largest, to an edge of the opening of the base part.

5. The radiation-irradiation device according to claim 3, wherein the contact member is formed of a columnar member and the interval ensuring unit includes a columnar connection member that connects the contact member to the base part, and the connection member is disposed on a plane formed by extending a lower surface of a housing of the radiation generating unit in the direction of the optical axis of the radiation in a case in which the interval ensuring unit is installed on the collimator unit so that an extending direction of the contact member is a vertical direction.

6. The radiation-irradiation device according to claim 1, wherein the interval ensuring unit is adapted to be detachably mounted on the collimator unit by magnets.

7. The radiation-irradiation device according to claim 1, further comprising:
an emission control unit that stops emission of the radiation in a case in which the interval ensuring unit is detached from the collimator unit.

* * * * *